United States Patent
Langford et al.

(10) Patent No.: US 10,226,287 B2
(45) Date of Patent: Mar. 12, 2019

(54) BONE PLATE WITH VERSATILE SCREW HOLES

(71) Applicant: Core Orthopaedics, Inc., North Bay Village, FL (US)

(72) Inventors: Joshua Langford, Orlando, FL (US); Kenneth West, Flagler Beach, FL (US)

(73) Assignee: Association for the Advancement of Musculoskeletal, Ponte Verde Beach, FL (US)

( * ) Notice: Subject to any disclaimer, the term of this patent is extended or adjusted under 35 U.S.C. 154(b) by 489 days.

(21) Appl. No.: 14/580,613

(22) Filed: Dec. 23, 2014

(65) Prior Publication Data
US 2015/0272638 A1 Oct. 1, 2015

Related U.S. Application Data

(60) Provisional application No. 61/972,681, filed on Mar. 31, 2014.

(51) Int. Cl.
*A61B 17/80* (2006.01)
*A61B 17/17* (2006.01)

(52) U.S. Cl.
CPC ...... *A61B 17/8014* (2013.01); *A61B 17/1728* (2013.01)

(58) Field of Classification Search
CPC .................. A61B 17/8014; A61B 17/8004
See application file for complete search history.

(56) References Cited

U.S. PATENT DOCUMENTS

| | | |
|---|---|---|
| 5,709,686 A | 1/1998 | Talos et al. |
| 6,669,701 B2 | 12/2003 | Steiner et al. |
| 6,719,759 B2 | 4/2004 | Wagner et al. |
| 6,730,091 B1 | 5/2004 | Pfefferle et al. |
| 7,179,260 B2 | 2/2007 | Gerlach et al. |
| 7,354,441 B2 | 4/2008 | Frigg |
| 7,655,029 B2 | 2/2010 | Niederberger et al. |
| 7,695,472 B2 | 4/2010 | Young |
| 7,722,653 B2 | 5/2010 | Young et al. |
| 7,740,648 B2 | 6/2010 | Young et al. |
| 7,776,076 B2 | 8/2010 | Grady, Jr. et al. |
| 7,905,910 B2 | 3/2011 | Gerlach et al. |
| 7,909,858 B2 | 3/2011 | Gerlach et al. |
| 7,951,176 B2 | 5/2011 | Grady et al. |
| 7,951,178 B2 | 5/2011 | Jensen |
| 7,976,570 B2 | 7/2011 | Wagner et al. |
| 8,246,661 B2 | 8/2012 | Beutter et al. |
| 8,317,846 B2 | 11/2012 | Bottlang |
| 8,460,344 B2 | 6/2013 | Niederberger et al. |
| 2005/0107796 A1 | 5/2005 | Gerlach et al. |
| 2006/0129151 A1 | 6/2006 | Allen et al. |
| 2007/0233106 A1 | 10/2007 | Horan et al. |

(Continued)

*Primary Examiner* — Zade Coley
*Assistant Examiner* — Olivia C Chang
(74) *Attorney, Agent, or Firm* — Farber LLC; Tram Anh Nguyen

(57) ABSTRACT

A bone plate for the compression of a fracture site or osteotomy of a bone includes a bone plate body having a plurality of screw holes and bone screws accommodated in the screw holes. At least one of the screw holes is teardrop shaped having a wide portion and a narrow portion. The bone screw selected for use in the screw hole can be either a locking screw or a non-locking screw, as the screw hole can accept both types.

15 Claims, 5 Drawing Sheets

(56) References Cited

U.S. PATENT DOCUMENTS

| | | |
|---|---|---|
| 2008/0058815 A1 | 3/2008 | Young |
| 2008/0119894 A1 | 5/2008 | Ehrhardt et al. |
| 2008/0132955 A1 | 6/2008 | Frigg |
| 2008/0140130 A1 | 6/2008 | Chan et al. |
| 2008/0161860 A1* | 7/2008 | Ahrens .............. A61B 17/1728 606/280 |
| 2008/0234749 A1 | 9/2008 | Forstein |
| 2009/0024172 A1 | 1/2009 | Pizzicara |
| 2010/0057086 A1 | 3/2010 | Price et al. |
| 2010/0274247 A1 | 10/2010 | Grady, Jr. et al. |
| 2010/0305570 A1 | 12/2010 | Sarangapani et al. |
| 2011/0184414 A1 | 7/2011 | Andermahr et al. |
| 2011/0202093 A1 | 8/2011 | Grady, Jr. et al. |
| 2011/0264149 A1* | 10/2011 | Pappalardo ........ A61B 17/8019 606/286 |
| 2011/0282393 A1 | 11/2011 | Gerlach et al. |
| 2011/0295325 A1 | 12/2011 | Wagner et al. |
| 2012/0123484 A1 | 5/2012 | Lietz et al. |
| 2012/0197307 A1 | 8/2012 | Fritzinger et al. |
| 2012/0265254 A1 | 10/2012 | Horan et al. |
| 2012/0265255 A1 | 10/2012 | Hilse et al. |
| 2013/0150901 A1 | 6/2013 | Kortenbach et al. |

\* cited by examiner

BONE PLATE WITH VERSATILE SCREW HOLES

CROSS-REFERENCE TO RELATED APPLICATIONS

This application claims benefit of U.S. Provisional Application No. 61/972,681 filed Mar. 31, 2014, and entitled "Bone Plate with Versatile Screw Holes," the contents of which are incorporated herein by reference in their entirety.

FIELD OF THE INVENTION

The present invention relates to orthopedic internal fixation devices, and more particularly to a bone plate for fixation and compression. The bone plate contains versatile screw holes that can accept both locking and non-locking bone screws to effect fixation and/or compression to heal a bone fracture.

BACKGROUND OF THE INVENTION

Bone fractures can occur due to a number of reasons: disease, such as osteoporosis; overuse by repetitive motion, which can, for example, cause stress fractures in athletes; trauma, such as by a fall or car accident; and the physiological changes that come with the aging process. An osteotomy is a surgical operation in which a bone is excised to shorten, lengthen or change the alignment of the bone. Osteotomies are often performed to correct bone deformities. Proper healing of both bone fractures and osteotomies can involve open reduction and internal fixation, where the bone fragments are repositioned in their normal alignment and then held together to facilitate healing.

A bone plate is a type of internal fixator that is surgically implanted and may generally be used to stabilize bone fragments and carry out osteosynthesis. For non-unions, such as joint fractures, simple shaft fractures and osteotomies, it is desirable that the bone itself supports and stabilizes rigid osteosynthesis. In cases of comminuted fractures, it is desirable that the bone ends be aligned and stabilized, while the proper length of the bone is maintained in flexible osteosynthesis.

Bone plates are often used to aid in the treatment of different bone fractures and osteotomies. Bone fractures, however, can be complicated, requiring treatment with more than one type of osteosynthesis. In one design, a bone plate can have a first set of holes for non-locking screws to achieve compression of the fracture site, and a second set of holes for locking screws to achieve fixed-angle fixation. One drawback of this type of plate is that it requires a large number of holes in the plate, which weakens the plate or requires a larger or thicker plate to compensate. In another design, a bone plate can have a combination of types of holes in a predetermined arrangement for receiving a locking screw or a non-locking screw. This plate still has the drawback of limiting the user to the type of receiving screw holes on the plate. In other words, certain parts of the bone plate can receive a locking screw for fixation, while other parts of the bone plate can receive a non-locking screw for compression. The user is not able to modify the location of the non-locking versus locking screws relative to the plate, and may have to utilize two or more plates to achieve the desired effect.

In general, bone plates may be utilized to carry out two different types of osteosynthesis, namely "rigid osteosynthesis" and "flexible osteosynthesis." Rigid osteosynthesis is used for medical care of joint fractures, simple shaft fractures (where nailing is impossible) as well as for osteotomies. Aside from the possibility of anatomical repositioning, the bone itself supports and stabilizes the osteosynthesis, which allows for the possibility of putting stress on the extremity earlier and without pain. Additional advantages of the medical care of stable fractures can be observed when the blood circulation in the bone is greatly diminished due to trauma. For treating "nonunions" or in the case of existing infection, the fracture must be kept stable in order to make bone healing possible and so as not to irritate the infection further by instability of the fracture gap.

Flexible osteosynthesis, also known as "biological osteosynthesis," may be desirable in the medical treatment of comminuted fractures in the shaft region of tubular bones. In the case of these fractures, it is an objective to maintain the proper length of the bone and to fix the bone ends (joints) in their proper anatomic positions with respect to one another. With flexible osteosynthesis, the fracture zone is not directly affixed or manipulated, and consequently, the blood circulation in this area is not inhibited. Bone plates designed for flexible osteosynthesis thus operate similarly to a locking, intramedullary nail, which is anchored only in the metaphyses.

Since fractures cannot always be treated with one type of osteosynthesis, surgeons must frequently compromise because a bone plate, which allows him to combine the two types of osteosynthesis discussed above, is not currently available. Such a combination would be beneficial, for example, when a joint fracture can be compressed with traction screws through the bone plate and the whole of the joint may be connected to the diaphysis over an internal fixative with angularly stable screws. Another illustrative application concerns porotic bones, where a bone plate with axially and angularly stable screws can be anchored in the metaphysial fragment, with a stable plate-affixation being undertaken in the diaphyseal range with the assistance of a plate traction screw through the fracture. A primary fracture stabilization can be achieved by this type of procedure.

This situation has led to the development and marketing of bone fracture fixators for both types of osteosynthesis. The two types of fixators, however, are designed specifically for their respective method. Thus, the disadvantages of these two systems lie in the difficulty in combining them. Accordingly, it is desirable to provide improved bone plates that allow for both rigid and flexible osteosynthesis. More importantly, what is needed is a bone plate that allows for use of both non-locking and locking screws within the same bone screw hole, in order to allow either fixation or compression, or both, at different locations on the same bone plate.

BRIEF SUMMARY OF THE INVENTION

The present disclosure provides a bone plate for the compression of a fracture site or osteotomy of a bone wherein either a locking screw or a non-locking screw may be selected for use within the same screw hole to affect axial compression. This allows the surgeon to take into account the location, health and quality of the bone at the site when selecting the bone screw. If a locking screw is used, the fixation function and the compression function within the screw hole are performed simultaneously. For the patient, these structural and functional elements provide a number of advantages. The number of bone screws used to treat the fracture can be greatly reduced, which means the bone is perforated less and the surgery can be simplified. Also, fewer holes in the plate mean that the dimensions of the bone plate can be reduced while maintaining strength. In addition, as the holes take up less space in the plate, they and their respective bone screws, can be spaced closer together, which allows for increased fixation to provide a stable environment for healing to occur.

In one embodiment, the bone plate comprises a plate body having an upper surface, a lower, bone-contacting surface, and a plurality of screw holes extending between the upper surface and the lower surface. The screw holes may be located along the longitudinal axis of the plate. Bone screws having a tapered head and threaded shaft may be used in the screw holes to effect fixation and/or compression. At least one of the screw holes has a smooth contoured opening at the upper surface that is wider than the opening at the lower surface. The at least one screw hole may include a main chamber extending into a narrower portion to form a teardrop shaped screw hole opening, the main chamber wide portion including a partial circular hole, and the narrower portion extending from the main chamber along a longitudinal axis of the plate body in a direction away from a mid-line axis of the plate body. In one aspect, the wide portion may be a partial circular hole having a beveled edge and a threaded side, and the narrow portion may be non-threaded and extend from the wide portion along the longitudinal axis of the plate in a direction away from the mid-line axis of the plate. The wide portion or main chamber accepts both locking screws and non-locking screws and the narrow portion provides as a compression notch. As screwing of the bone screw into the bone proceeds through a final stage, engagement of the screw in the screw hole effects relative longitudinal displacement between the plate and the bone (i.e. axial compression). Selection of a locking screw further allows simultaneous fixed angle fixation and compression of the fracture or osteotomy with use of a single screw in a single screw hole. An advantage of this versatile hole design over the prior art is that compression of the fracture or osteotomy can be obtained while using any style screw, locking or non-locking, providing the surgeon flexibility to select a screw that is most appropriate for the location, health and quality of bone. For example, the option to use a locking screw in soft or osteopenic bone to obtain compression is particularly advantageous.

The present invention is also directed to a bone plating system including at least one bone plate, at least one locking bone screw and least one non-locking bone screw. The bone plate has at least one versatile screw hole that can accommodate both types of bone screws to affect axial compression of the bone, as well as fixation, if so desired. A drill guide may also be provided to cooperate with the bone plate and direct a drill bit into the narrow portion or compression notch of the screw hole to allow insertion of the screw.

The present invention is also directed to a method of affecting axial compression of a fracture site or osteotomy of a bone. The above-described bone plating system is used, wherein the surgeon selects either the locking screw or non-locking screw for use in the teardrop shaped screw hole based on the location, health and quality of the bone at the site.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 3A-3D illustrate an exemplary method of using the bone plate system of FIG. 1, in which:

FIG. 3A illustrates the bone plate system of FIG. 1 in use with a drill guide instrument and drill bit of the present invention.

FIG. 3B is an enlarged perspective view of the bone plate, drill guide instrument and drill bit of FIG. 3A in use.

FIG. 3C shows a cross-sectional view of the bone plate of FIG. 3B in use.

FIG. 3D shows a cross-sectional view of the bone plate with bone screw partially inserted.

The foregoing and other features of the present disclosure will become apparent to one skilled in the art to which the present disclosure relates upon consideration of the following description of exemplary embodiments with reference to the accompanying drawings.

DETAILED DESCRIPTION OF THE EMBODIMENTS

The embodiments provide a bone plate having a plurality of versatile screw holes that can accommodate either a locking or non-locking screw for the compression and/or fixation of a fracture site or osteotomy of a bone. Each of the versatile screw holes allows a statically placed threaded locking screw to provide both compression and fixation (i.e., locking). However, these versatile screw holes are also able to receive a non-locking screw, such as a cortex or cancellous screw, which would allow the screw to displace the plate upon insertion and achieve compression without locking. This offers the plate the advantage of providing a single screw opening that accommodates both types of screws (i.e., both locking and non-locking).

Figure 1:
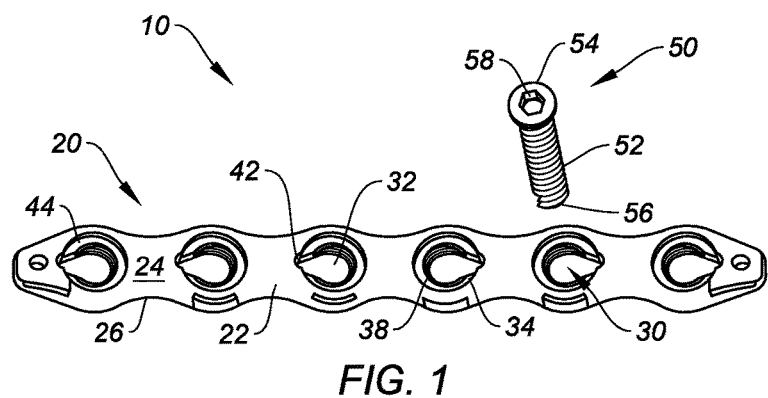
FIG. 1 is an exploded view of an exemplary embodiment of a bone plate system comprising a bone plate and a bone screw of the present invention.
Figure 2:
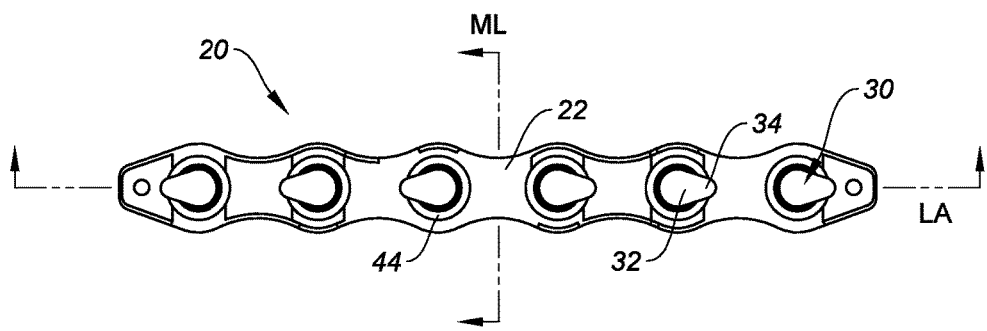
FIG. 2 is a top-down view of the bone plate of FIG. 1.

Turning now to the drawings, FIG. 1 shows an exemplary embodiment of a bone plate system 10 of the present invention. The system 10 may comprise a bone plate 20 and a bone screw 50 for the compression of a fracture site of a bone. The bone plate 20 can comprise a plate body 22 with at least two opposing screw holes 30, with one hole on each side of a mid-line axis ML of the plate body 22, as shown in FIG. 2. The screw holes 30 extend through and connect an upper surface 24 and a bone-contacting surface 26 of the plate body 22. These screw holes 30 are located on a common longitudinal axis LA of the plate body 22.

In the embodiments shown, two sets of directionally opposing screw holes 30 are equidistantly located along the plate body 22, however it is understood that the embodiments are not limited to this arrangement. For example, the bone plate 20 may include a single screw hole, two screw holes, or more than the six screw holes 30 depicted in the exemplary embodiment shown. A set of screw holes 30 may be oriented in one direction relative to the mid-line axis ML, with the other set of screw holes 30 facing an opposite direction relative to the midline axis ML, as shown. The sets may contain the same number of screw holes 30, or one set may have a different number of screw holes 30 than the other set.

Furthermore, although the bone plate 20 is shown as a straight rectangular bar, other configurations of the bone plate 20 are also encompassed by the invention. As the number of screw holes and spacings therebetween can vary, so can the shape of the plate body 22 without departing from the spirit of the invention. The plate body 22 can also have a curvature that is matched to the shape and design of the bone parts to be treated. For example, in one embodiment, the plate body 22 may be shaped like an "X", "+" or a "T", while in other embodiments, the plate body 22 may take the form of a diamond or square.

The bone plate 20 of the present invention is configured to receive bone screws 50 within these screw holes 30. An exemplary embodiment of a bone screw 50 is shown in FIG. 1. The bone screw 50 may include a head 54 with a tool-engaging opening 58, a threaded shaft 52, and a tip 56. The bone screw 50 can be either locking, whereby the head 54 is threaded, or non-locking, whereby the head 54 is not threaded. This head 54 may be tapered, with a curved underside.

In accordance with the invention, the screw holes 30 are versatile, and can accommodate either a locking or non-locking bone screw 50. In an exemplary embodiment, the screw hole 30 may be configured with a teardrop shaped geometry, as shown. The versatile screw hole 30 may comprise a main chamber represented by a wider portion 32 of the screw hole 30, which flows into a narrower portion 34. The wider portion 32 may be a partial circular hole having a beveled edge 44 extending from the upper surface 24, and a threaded side 38 extending from the bone-contacting surface 26. This threaded side 38 is angled such that the diameter of the screw hole 30 at the upper surface 24 is larger than the diameter of the screw hole 30 at the lower, bone-contacting surface 26. In cross-section, the threaded side 38 appears conical and forms one side of a cone or V-shaped channel (not shown).

The narrower portion 34 may be non-threaded and include a compression notch 42, and extend from the wide portion 32 along the longitudinal axis LA of the plate body 22 in a direction away from the mid-line axis ML of the plate body 22. As shown, only the curved distal end of the narrower portion 34 extends from the beveled edge 44, resulting in a groove 42 in the upper surface 24. The groove 42 has a radius that is smaller than the radius of the circular hole of the main chamber, or wider portion 32. As shown in FIG. 2, the combination of the wider portion or main chamber 32 and the narrower portion or compression notch 34 creates a screw hole 30 that is teardrop shaped. The narrower portion 34 opens into the main chamber 32 in a smooth transition to form a continuous curved opening, as can be seen in the top-down view of FIG. 2. The main chamber 32 of the screw hole 30 accepts both locking bone screws with threaded heads and non-locking bone screws with non-threaded heads.

Figure 3A:
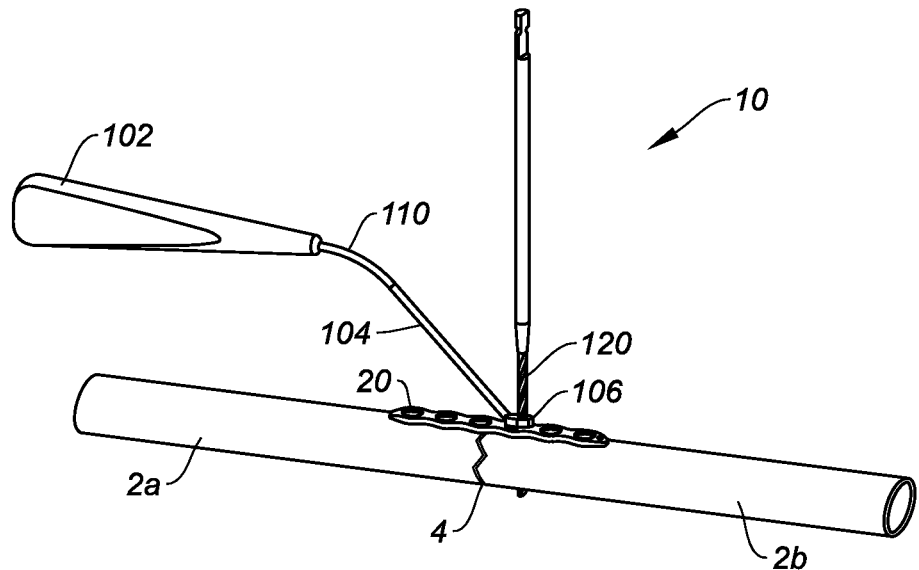
Figure 3B:
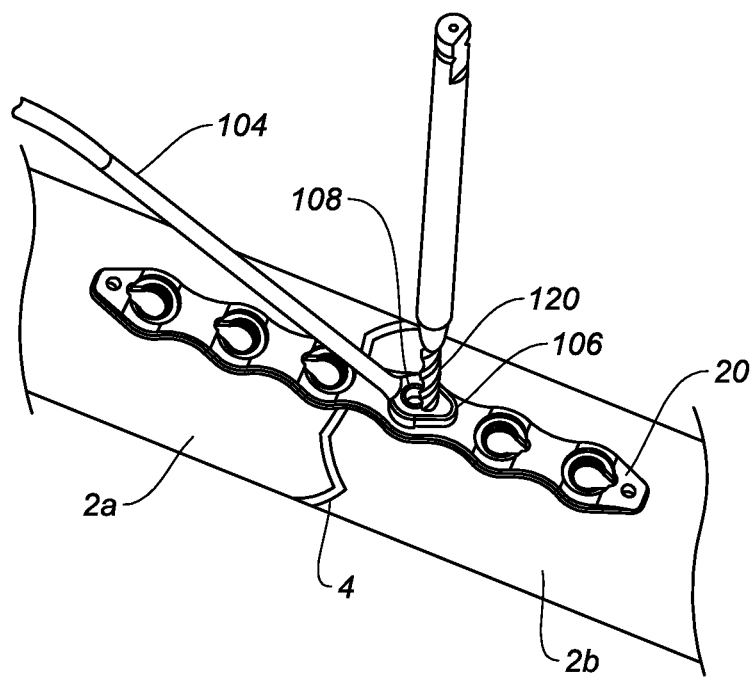
Figure 3C:
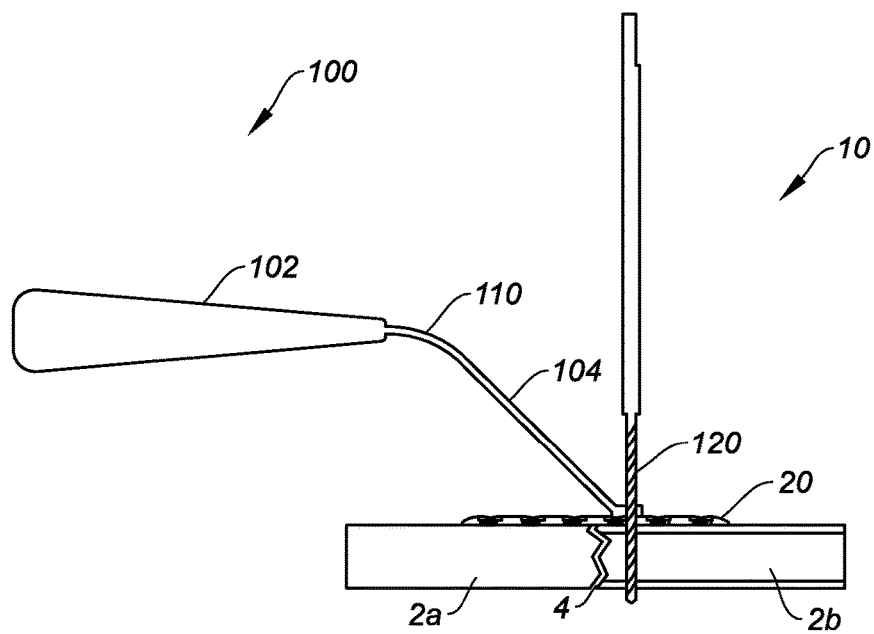
Figure 3D:
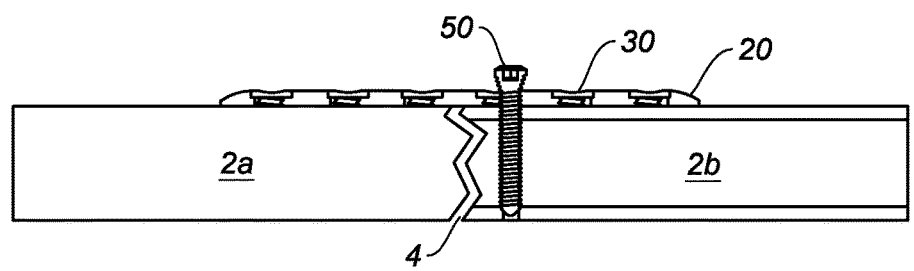

FIGS. 3A-3D illustrate an exemplary embodiment of a method of using the bone plate system 10 of the present invention to treat a bone fracture 4 between two bone segments 2a, 2b. As shown in FIG. 3A, the system 10 may further include a drill guide instrument 100 having a handle 102, an elongated shaft 104, and a guide plate 106. The shaft 104 may have a bent neck 110 to allow the instrument 100 to be held away from the working site. The guide plate 106 may have a shaped opening 108 that complements the teardrop shape of the versatile screw hole 30 of the bone plate 22. The shaped opening 108 of the drill guide instrument 100 assists the user to drill through the narrower portion or compression notch 34 portion of the screw hole 30, as shown in FIG. 3B. A pilot hole may be drilled prior to insertion of the bone screw 50, or alternatively, the bone screw 50 may be screwed directly into the bone. The pilot hole may be drilled using a standard drill bit 120 straight down the narrower portion or compression notch 34 of the screw hole 30, or the offset portion of the main chamber 32, as shown in FIG. 3C. Afterwards, the bone screw 50 may be inserted until partially tight, as illustrated in FIG. 3D.

A bone screw 50 is inserted into the pilot hole and screwed into bone using a tool (not shown) that cooperates with the tool-engaging opening 58 in the screw head 54. The threaded shaft 52 engages the threaded side 38 of the wider portion 32 of the screw hole 30. As the bone screw 50 is fully screwed into the bone and the tapered screw head 54 engages the beveled edge 44, the narrower portion 34 provides a compression notch 42, effecting relative longitudinal displacement between the plate 20 and the bone and thereby compressing the fracture or osteotomy. If a locking screw is selected for use in the screw hole 30, fixed angle fixation and compression occur simultaneously. An advantage of this teardrop shaped hole design over the prior art is that compression of the fracture or osteotomy can be obtained while using any style screw, locking or non-locking, providing the surgeon flexibility to select a screw that is most appropriate for the location, health and quality of bone. For example, the option to use a locking screw in soft or osteopenic bone to obtain compression is particularly advantageous.

In other words, in one manner of use, the main chamber 32 represents the area where the drill bit will be introduced when drilling the inner diameter of a cortex, cancellous or locking screw, which may have threaded heads or a smooth radius. The narrower portion 34 along with the compression notch 42 provides the compression area. As the drill bit makes contact with this compression area, the symmetry of the compression area ensures that the drill bit is contacted in two spots, which will balance and center the drill bit in the appropriate plane for compression or locking to occur.

Figure 4A:
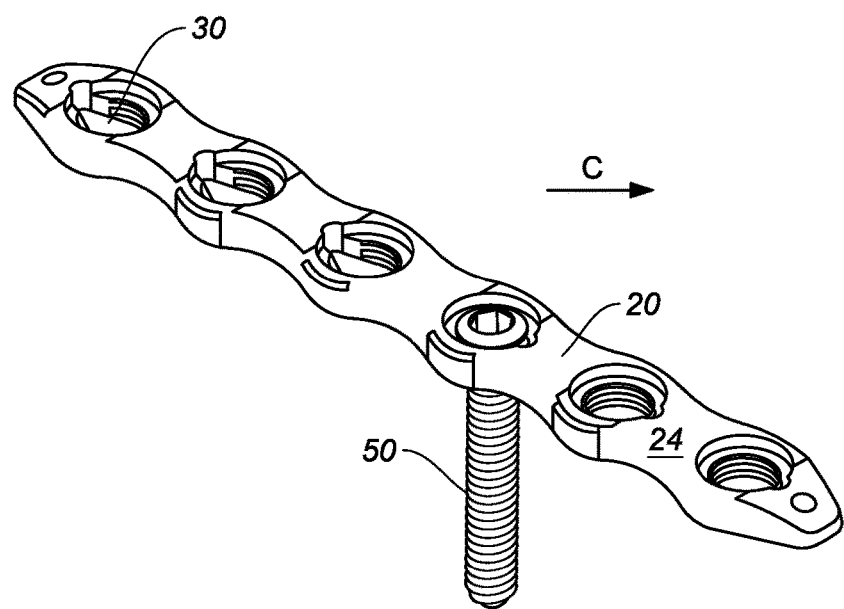
FIG. 4A shows a perspective view of the bone plate with a fully seated bone screw of FIG. 1.
Figure 4B:
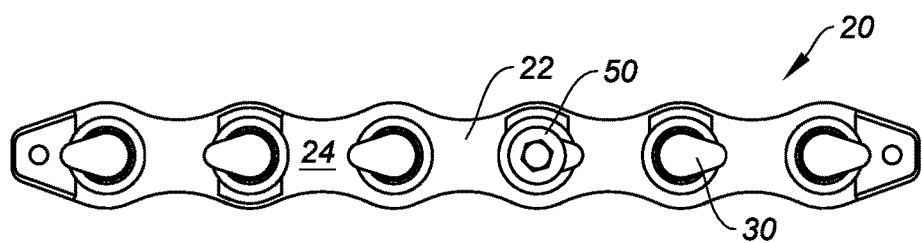
FIG. 4B is a top-down view of the bone plate with fully seated bone screw of FIG. 4A.
Figure 4C:
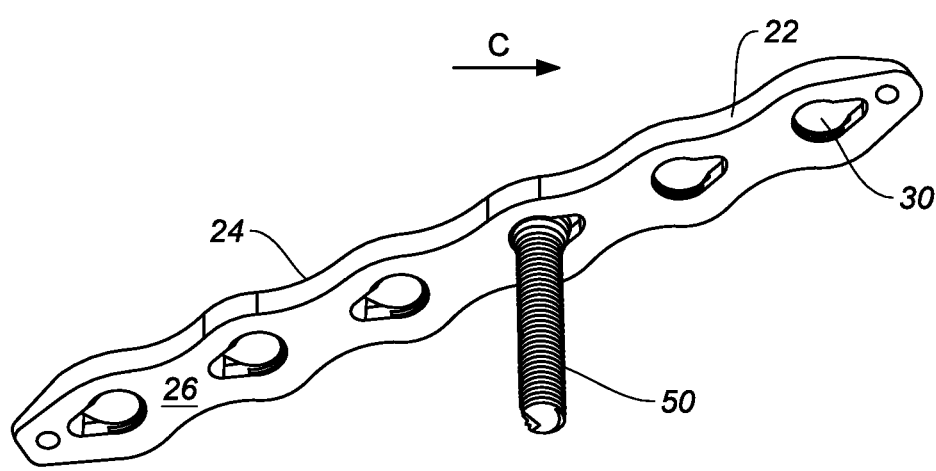
FIG. 4C is a bottom view of the bone plate with fully seated bone screw of FIG. 4A.

Upon tightening the bone screw 50 into the screw hole 30, the underside of the screw head 54 will eventually make contact with the plate 20, and in particular the beveled edge 44 of the screw hole 30. As the screw 50 advances and engages the threaded side 38 of the main chamber 32, the plate 20 will shift such that the bone screw 50 appears centered relative to the main chamber 32, as shown in FIGS. 4A and 4B. The plate 20 shifts to the right in the direction of arrow C, representing the entire distance of the underside of the bone screw 50. The bone screw 50 is fully seated when it is centered relative to the main chamber 32, as shown in FIGS. 4A-4C. Accordingly, compression of the fracture 4 is achieved. When a non-locking screw is used (i.e., without threads on the underside of the screw head 54), the screw is not locked and yet still allows compression of the fracture 4 to bring together bone segments 2a, 2b. Where both compression and locking is desired, of course it is understood that a locking screw may just as easily be applied in the same screw hole 30 in the same manner described above. In one embodiment, the bone screw 50 travels approximately 1 mm, equal to the distance of the outer diameter (OD) of the screw threads and the top of the screw head 54.

Another way to describe the process of fixing and/or compressing a fracture is as follows: (a) reduce the fracture 4; (b) size the appropriate bone plate 20; (c) span the fracture 4 with the plate 20, usually with equal amounts of screws 50 on each side of the fracture 4, though not always; (d) drill a pilot hole using a drill bit 120 and the drill guide instrument 100 near the compression notch 42 at the narrower portion 34 of the screw hole 30; (e) place a bone screw 50 into the pilot hole until semi-tight; (f) repeat steps (d) and (e) until all screw holes 30 are filled; and (g) tighten each bone screw 50 to effect compression of the fracture 4. If locking screws are used, then both compression and fixation will be achieved. If non-locking screws are used, then only compression is achieved.

Preferred materials for the bone plate and the bone screw are preferably biocompatible materials such as titanium, titanium alloys, steel, cobalt chromium alloys, plastic or composites. According to the invention, the bone plate and the bone screw can also be made of different materials having different mechanical properties.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A bone plate for the compression of a bone fracture or osteotomy, comprising:
    a plate body with an upper surface, a bone contacting lower surface, and at least one screw hole extending between the upper surface and the lower surface, the at least one screw hole having a smooth contoured opening at the upper surface that is wider than an opening at the lower surface, the at least one screw hole including a main chamber extending into a narrower portion to form a teardrop shaped screw hole opening, the main chamber including a partial circular hole having a beveled edge extending from the upper surface, and the narrower portion extending from the main chamber along a longitudinal axis of the plate body in a direction away from a mid-line axis of the plate body, the narrower portion extending into a compression notch having a smooth, rounded sidewall extending between the upper and lower surfaces, only a curved distal end of the narrower portion extending from the beveled edge to form a groove in the upper surface, the groove extending outwardly along the longitudinal axis such that the screw hole is shaped by two partially overlapping circles, the smooth contoured opening of the at least one screw hole further having a substantially circular shape at the upper-most surface of the plate body;
    wherein the at least one screw hole is configured to accept a locking bone screw or a non-locking bone screw, the at least one screw hole further being configured to affect axial compression when the bone screw is fully engaged.

2. The bone plate of claim 1, wherein the beveled edge is configured to engage a head of the bone screw.

3. The bone plate of claim 1, wherein the main chamber has a threaded side extending from the bone-contacting lower surface, the threaded side being configured to engage a threaded shaft of the bone screw.

4. The bone plate of claim 3, wherein the screw hole is conical.

5. The bone plate of claim 1, wherein the narrower portion is non-threaded.

6. The bone plate of claim 1, wherein the screw hole is configured to affect fixed angle fixation at the same time as axial compression when used with a locking screw.

7. The bone plate of claim 1, further including a plurality of screw holes.

8. The bone plate of claim 7, wherein the screw holes are equidistantly space relative to a mid-line axis of the bone plate.

9. The bone plate of claim 7, wherein one set of screw holes is configured to face in a directionally opposite direction to another set of screw holes.

10. A bone plate system for the compression of a bone fracture or osteotomy, comprising:
    a bone plate having a plate body with an upper surface, a bone contacting lower surface, and at least one screw hole extending between the upper surface and the lower surface, the at least one screw hole having a smooth contoured opening at the upper surface that is wider than an opening at the bone-contacting lower surface, the smooth contoured opening of the at least one screw hole further having a substantially circular shape at the upper-most surface of the plate body, the at least one screw hole including a main chamber extending into a narrower portion to form a teardrop shaped screw hole opening, the main chamber including a partial circular hole having a beveled edge extending from the upper surface, and the narrower portion extending from the main chamber along a longitudinal axis of the plate body in a direction away from a mid-line axis of the plate body, the narrower portion further extending into a compression notch having a smooth, rounded sidewall extending between the upper and lower surfaces, only a curved distal end of the narrower portion extending from the beveled edge to form a groove in the upper surface, the groove extending outwardly along the longitudinal axis such that the screw hole is shaped by two partially overlapping circles, the at least one screw hole being configured to accept a locking bone screw or a non-locking bone screw, the at least one screw hole further being configured to affect axial compression when the bone screw is fully engaged; and a bone screw comprising a tapered head extending into an elongated shaft and terminating in a tip, the elongated shaft including threads and the tapered head having a contoured underside.

11. The system of claim 10, wherein beveled edge is configured to contact the underside of the bone screw and angularly urge the screw during insertion.

12. The system of claim 10, wherein the tapered head of the bone screw includes threads.

13. The system of claim 12, wherein the main chamber includes a threaded side for engaging the threads of the tapered head of the bone screw during insertion.

14. The system of claim 10, wherein the contoured underside of the bone screw is smooth.

15. The system of claim 10, further including a drill guide instrument comprising a handle, an elongated shaft, and a guide plate, the guide plate having a teardrop shaped opening that complements the shape and size of the at least one screw hole.

* * * * *

UNITED STATES PATENT AND TRADEMARK OFFICE
CERTIFICATE OF CORRECTION

PATENT NO. : 10,226,287 B2
APPLICATION NO. : 14/580613
DATED : March 12, 2019
INVENTOR(S) : Joshua Langford et al.

Page 1 of 1

It is certified that error appears in the above-identified patent and that said Letters Patent is hereby corrected as shown below:

On the Title Page

In the Applicant (71):
Change "Core Orthopaedics, Inc." to --ASSOCIATION FOR THE ADVANCEMENT OF MUSCULOSKELETAL INNOVATION, INC.--

In the Assignee (73):
Change "ASSOCIATION FOR THE ADVANCEMENT OF MUSCULOSKELETAL" to --ASSOCIATION FOR THE ADVANCEMENT OF MUSCULOSKELETAL INNOVATION, INC.--

Signed and Sealed this
Thirty-first Day of December, 2019

Andrei Iancu
*Director of the United States Patent and Trademark Office*